United States Patent [19]

Webb

[11] Patent Number: 5,578,050
[45] Date of Patent: Nov. 26, 1996

[54] ERGONOMIC SURGICAL SCALPEL SLEEVE

[76] Inventor: Nicholas J. Webb, 5370 Basel Dr., Box 831, Wrightwood, Calif. 92397

[21] Appl. No.: 222,601

[22] Filed: Apr. 4, 1994

[51] Int. Cl.⁶ ................................................ A61D 17/00
[52] U.S. Cl. ................................ 606/167; 606/1; 606/170; 16/111 R
[58] Field of Search .................................... 606/166, 167; 30/329, 340; 16/DIG. 12, 111 R

[56] References Cited

U.S. PATENT DOCUMENTS

| | | | |
|---|---|---|---|
| 4,414,974 | 11/1983 | Dotson et al. | 606/167 |
| 4,576,164 | 3/1986 | Richeson | 606/167 |
| 5,309,641 | 5/1994 | Wonderley et al. | 606/167 |
| 5,312,429 | 5/1994 | Noack | 606/167 |
| 5,417,704 | 5/1995 | Wonderley | 606/167 |

*Primary Examiner*—Michael Powell Buiz
*Assistant Examiner*—William Lewis
*Attorney, Agent, or Firm*—Lyon & Lyon

[57] ABSTRACT

A handle sleeve for facilitating the use of ophthalmic and micro-surgical instruments such as scalpels includes a flexible tube which can be removably attached to the instrument handle. The sleeve preferably has a knurling pattern or a plurality of ridges disposed on its outside surface, to improve traction and tactile feel. The sleeve provides a superior gripping surface and significantly reduces the force necessary for the surgeon to maintain dynamic control of the instrument during surgical procedures, and also reduces stress associated with repetitive movement injury and cumulative trauma disorder.

16 Claims, 2 Drawing Sheets

ERGONOMIC SURGICAL SCALPEL SLEEVE

BACKGROUND OF THE INVENTION

This invention relates to ergonomic sleeves for surgical scalpels, and particularly scalpels used in ophthalmic and microsurgery.

Conventional surgical scalpels used in microsurgery typically have a plastic handle portion and a blade attached to the handle. These conventional scalpels often have several drawbacks when used in very precise procedures such as ophthalmic surgery. First, studies indicate that the use of conventional scalpels can result in repetitive motion injuries to the hands and wrists of microsurgeons due to the repetitive movements involved in microsurgery. Additionally, conventional scalpel handles provide inadequate tactile control for certain microsurgical procedures. Further, the smooth surfaces of conventional scalpel handles requires surgeons to expend energy squeezing the handle with his or her fingers to maintain adequate control of the scalpel while making incremental surgical movements.

Therefore, a need exists for a surgical scalpel handle which provides increased tactile control while reducing repetitive motion injuries and cumulative trauma disorder and while reducing the amount of pressure required to be exerted by the surgeon to maintain control of the scalpel.

SUMMARY OF THE INVENTION

The present invention provides an ergonomic sleeve for surgical scalpels preferably comprising a low durometer silicone or thermo-plastic sleeve having aggressive knurling or ridges formed on its outside surface. The sleeve is adapted to slide over and engage the handle of a surgical scalpel or similar instrument, to provide an improved gripping surface therefor.

BRIEF DESCRIPTION OF THE DRAWING FIGURES

FIG. 2b is a section view of the sleeve of FIG. 2a;

DETAILED DESCRIPTION OF THE PREFERRED EMBODIMENTS

Figure 1:
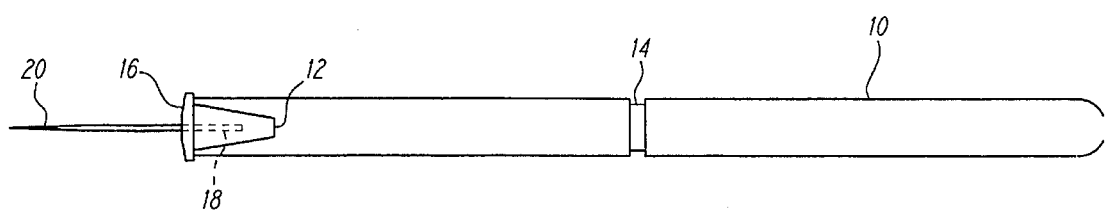
FIG. 1 depicts a particular surgical scalpel ("Ergoblade") with which the present invention may be used.

FIG. 1 depicts a handle apparatus for a microsurgical scalpel blade manufactured by Eagle Vision, Inc., Memphis, Tenn., under the commercial name "Ergoblade". The Ergoblade comprises an elongated central member 10 constructed of aluminum or other suitable thermoplastic materials, and having a hollowed distal portion 12. A slot 14 is located on the central member 10 and extends along the circumference of the central member in a lateral direction. A clam collet 16 incorporating a flat top slotted and circular component with a hinged collet assembly 18 provides a locking mechanism for a micro-surgical scalpel blade 20 into the hollowed distal portion 12 of the central member 10. The Ergoblade is adapted to engage a variety of micro-surgical scalpel blades having a uniform shank design within the clam collet assembly 16, to provide a surgical scalpel handle that can be re-used several times with different scalpel blades.

Figure 2A:
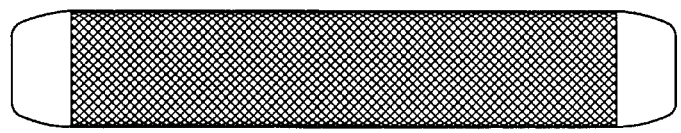
FIG. 2a depicts a sleeve according to the present invention.
Figure 2B:
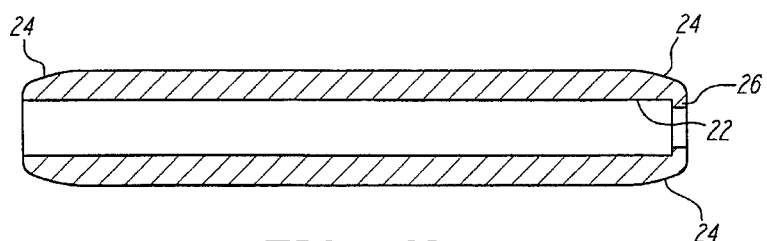

FIGS. 2a and 2b illustrate an ergonomic sleeve according to the present invention. FIG. 2a is a side view of a sleeve. The sleeve comprises a flexible, elongated tube open at both ends. FIG. 2b is a section view of the sleeve of FIG. 2a, illustrating the hollow interior of the sleeve and the inner surface thereof. The inner surface of the sleeve is generally designated as 22. In the preferred embodiment in which the sleeve is particularly adapted to fit onto an Ergoblade, the interior or inner surface 22 of the sleeve is substantially cylindrical in cross-section, to engage the cylindrical central member 10 of the Ergoblade. However, it should be apparent to those in the art that the inner surface of the sleeve may be molded in other configurations so that the sleeve may be adapted for other types of medical instrument configurations.

The sleeve is adapted to be positioned at the lower or distal portion of the elongated central member 10 of the Ergoblade by way of a friction fit. The sleeve has tapered end portions 24. The outer surface of the sleeve has formed thereon an aggressive raised knurling pattern.

The sleeve may be formed by way of transfer and/or injection molding, and is preferably formed of a low durometer silicone or thermo-plastic material, such as the materials sold under the commercial names C-flex or Kraton, although any other similar materials may be used. Preferably, the sleeve is formed of 40–60 durometer. The sleeve is also preferably constructed so that it may be sterilized and autoclaved so that a single sleeve may be used repeatedly.

When used with an Ergoblade as described above, the sleeve may also be formed with an inner ring 26 on the rearward end of the sleeve (shown as projecting portions in the section view of FIG. 2b). This inner ring 26 is formed on the circumference of the circular inner surface of the sleeve and projects inwardly from the inner surface of the sleeve so that, when the sleeve is in its proper location on the Ergoblade, the inner ring engages the slot 14 on the central member of the Ergoblade. The engagement of the inner ring 26 in the slot 14 helps to prevent moisture and surgical debris from entering the sleeve and becoming trapped between the sleeve and the Ergoblade handle, and also helps to hold the sleeve in place on the Ergoblade handle by preventing the sleeve from sliding longitudinally along the central member 10 during use.

Figure 3:
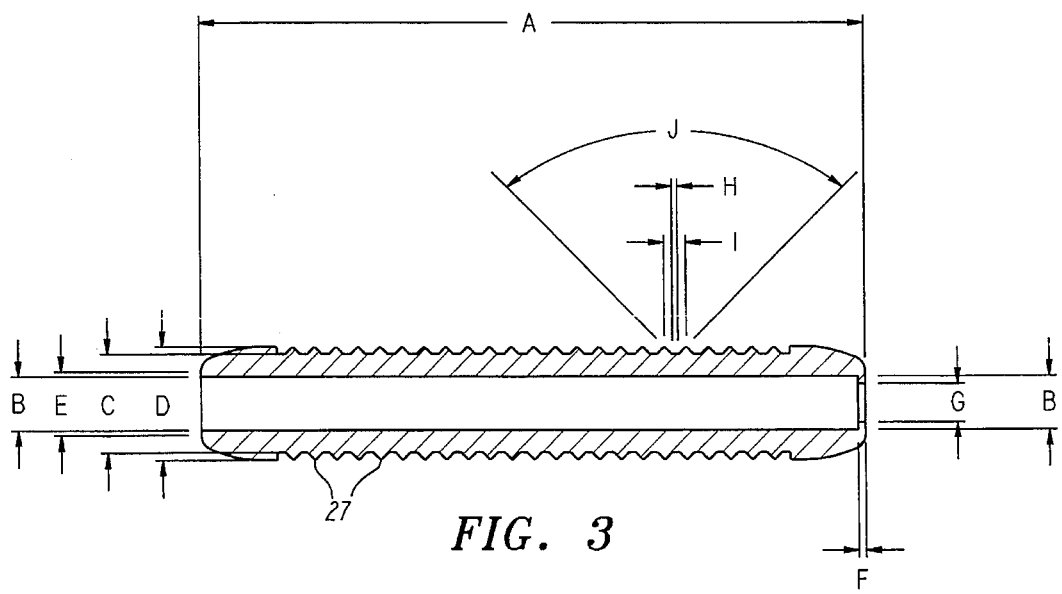
FIG. 3 is a section view of another embodiment of the present invention.
Figure 4A:
FIG. 4a depicts another embodiment of the present invention.
Figure 4B:
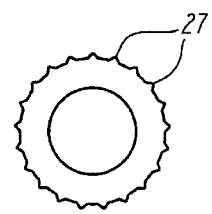
FIG. 4b depicts the embodiment of FIG. 4a, rotated 90 degrees.

FIG. 2a above shows one embodiment of the present invention in which a knurling pattern is formed on the outer surface of the sleeve. This knurling pattern provides increased tactile control of the instrument during use. FIGS. 3, 4a and 4b illustrate other preferred embodiments of the present invention, in which raised ridges 27 are formed on the outer surface instead of a knurling pattern. FIG. 3 shows a sleeve with a series of ridges 27 disposed laterally around the sleeve. FIGS. 4a and 4b show a sleeve with ridges 27 disposed longitudinally along the outer surface. To provide maximum tactile control, each of these ridges is triangular in cross-section (as is shown in FIG. 4b), although other configurations could be used. Preferably, each of these ridges is formed having dimensions indicated in FIG. 3 and discussed below.

In the preferred embodiment of the present invention, in which the sleeve is adapted to be used with an Ergoblade, the sleeve has the following approximate dimensions, corresponding to the portions of FIG. 3 identified with reference letters "A" through "J": The overall length "A" of the sleeve preferably is 2.3 inches; the diameter "B" of the hollow inner surface is 0.25 inches; the diameter "C" of the entire sleeve, measured from the base of the ridges, is 0.44 inches; the diameter "D" of the sleeve, as measured at its widest point (the tips of the ridges) is 0.50 inches; the diameter "E" of the sleeve, measured at the narrower ends of the tapering portions 24, is 0.38 inches; the thickness "F" of the inner ring 26 is 0.03 inches; the interior diameter "G" of the inner ring 26 is 0.19 inches; the distance "H" between the base of each ridge is 0.03 inches; the distance "I" between the apex or point of each triangular ridge is 0.09 inches; and the angle "J" formed by the sloping sides of adjacent ridges is 90 degrees. However, sleeves may be manufactured with other dimensions to provide different types of tactile feel or control. Further, these dimensions may be adjusted as necessary to adapt the sleeve for use with other types of medical instruments. In addition to scalpels such as the Ergoblade, the present invention is particularly suitable for use with a phaco-emulsification handpiece and with an infusion/aspiration (I/A) handpiece. The modifications necessary to adapt the sleeve to those applications will be readily apparent to those in the art and are within the scope of the present invention.

Figure 5:
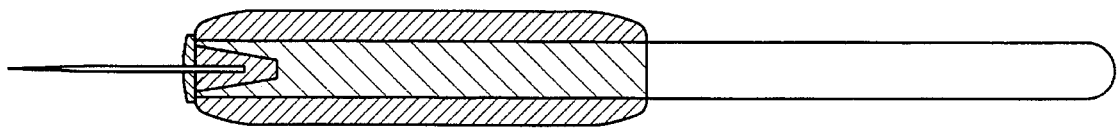
FIG. 5 shows a sleeve according to the present invention positioned in place on a surgical scalpel.

Prior to a surgical procedure, the sleeve is slid longitudinally onto the Ergoblade so that it frictionally engages the central member 10 at a distal portion thereof, corresponding to the portion of the central member normally grasped by the surgeon. FIG. 5 depicts a scalpel of the Ergoblade type with a sleeve engaged thereon. The surgeon then grasps the sleeve with the fingers of one hand to manipulate the scalpel. The tapered end portions 24 of the sleeve provide a smooth, comfortable transition to the central member and also provide a tighter fit between the sleeve and the handle or hand piece of the scalpel to minimize any space in the sleeve in which surgical debris such as human tissue or visco-elastic material may be caught. The knurling or ridged pattern on the outer surface of the sleeve improves traction and tactile feel, and significantly reduces the force necessary to maintain dynamic control of the surgical instrument or scalpel. The sleeve also absorbs movement energy and force, thereby reducing stress associated with repetitive movement injury and cumulative trauma disorder.

The Ergoblade may also be commercially manufactured and sold with the sleeve already in its proper place on the central member, so that the scalpel and sleeve are ready for use when removed from the packaging. The sleeve may also be left in place on the central member during sterilization.

As described above, in an alternative preferred embodiment of the present invention, the dimensions of the sleeve may be altered so that the sleeve can be used to aid in the grasping of a phaco-emulsification handpiece. Further, in yet another alternative preferred embodiment of the present invention, the dimensions of the sleeve may be adjusted so that the sleeve can be used to aid in the grasping of an infusion/aspiration (I/A) Handpiece. In both of these alternative embodiments, the sleeve comprises essentially the same components, except that the dimensions of the sleeve are increased or decreased to accommodate the desired applications, as will be readily apparent to those in the art. As will also be apparent to those in the art, the sleeve according to the present invention could also be modified or adapted to be used with any other medical or surgical instrument having an elongated portion which in operation is grasped and manipulated by the hand without departing from the spirit and scope of the present invention as set forth in the appended claims.

I claim:

1. A sleeve for a hand held surgical instrument comprising:

an elongated elastomeric tube including a low durometer thermoplastic material capable of deforming under fingertip pressure applied by the hand, said tube having an inner surface and an outer surface, and having openings on both ends thereof sized to receive the instrument into said tube so that said inner surface of said tube frictionally engages the instrument; and a raised pattern disposed on said outer surface of said tube.

2. The sleeve of claim 1 wherein said raised pattern disposed on said outer surface of said tube forms a substantially round perimeter.

3. The sleeve of claim 2 wherein said tube is tapered on said both ends thereof.

4. The sleeve of claim 2 further comprising a projecting portion disposed on said inner surface of said tube adapted to engage a slot on the instrument.

5. The sleeve of claim 1 wherein said tube is tapered on said both ends thereof.

6. The sleeve of claim 1 further comprising a projecting portion disposed on said inner surface of said tube and adapted to engage a slot on the instrument.

7. A sleeve for a hand held surgical instrument comprising:

an elongated elastomeric tube capable of deforming under fingertip pressure applied by the hand, said tube having an inner surface and an outer surface, and having openings on both ends thereof sized to receive the instrument into said tube so that said inner surface of said tube frictionally engages the instrument; and a raised pattern having a plurality of ridges on said outer surface of said tube wherein said raised pattern disposed on said outer surface of said tube forms a substantially round perimeter.

8. A sleeve for a hand held surgical instrument comprising:

an elongated elastomeric tube including a low durometer silicone capable of deforming under fingertip pressure applied by the hand, said tube having an inner surface and an outer surface, and having openings on both ends thereof sized to receive the instrument into said tube so that said inner surface of said tube frictionally engages the instrument; and a raised pattern disposed on said outer surface of said tube.

9. A sleeve for a hand held surgical instrument comprising:

an elongated elastomeric tube including a low durometer silicone capable of deforming under fingertip pressure applied by the hand, said tube having an inner surface and an outer surface, and having openings on both ends thereof sized to receive the instrument into said tube so that said inner surface of said tube frictionally engages the instrument; and a raised pattern having a plurality of ridges on said outer surface of said tube.

10. In a hand held surgical scalpel of the type having an elongated central member, the improvement comprising:

an elongated elastomeric sleeve around the central member including a low durometer thermoplastic material capable of deforming under fingertip pressure applied by the hand, said sleeve having an inner surface and an outer surface and having openings on both ends thereof sized to receive the elongated central member into said sleeve so that said inner surface of said sleeve frictionally engages the elongated central member; and a raised pattern disposed on said outer surface of said sleeve.

11. The surgical scalpel of claim 10 wherein said low durometer thermoplastic material is a material of between 40 and 60 durometer.

12. The surgical scalpel of claim 10 wherein the elongated central member further includes a hollowed distal portion, and a locking mechanism for removably engaging a scalpel blade.

13. In a hand held surgical scalpel of the type having an elongated central member, the improvement comprising:

an elongated elastomeric sleeve around the central member capable of deforming under fingertip pressure applied by the hand, said sleeve having an inner surface and an outer surface and having openings on both ends thereof sized to receive the elongated central member into said sleeve so that said inner surface of said sleeve frictionally engages the elongated central member and whereby said sleeve is capable of sliding onto and off of the central member for reuse; and a raised pattern disposed on said outer surface of said sleeve.

14. The surgical scalpel of claim 13 wherein the elongated central member further includes a hollowed distal portion, and a locking mechanism for removably engaging a scalpel blade.

15. In a surgical scalpel of the type having an elongated central member, the improvement comprising:

a flexible elongated elastomeric sleeve having a first tapered end and a second tapered end and including a low durometer thermoplastic material around the central member, said sleeve having an inner surface and an outer surface and having openings on both ends thereof sized to receive the elongated central member into said sleeve so that said inner surface of said sleeve frictionally engages the elongated central member, the inner surface of said sleeve having a projecting portion adapted to engage a slot disposed on the elongated central member; and a raised pattern disposed on said outer surface of said sleeve.

16. In a surgical scalpel of the type having an elongated central member, the improvement comprising:

a flexible elongated elastomeric sleeve having a first tapered end and a second tapered end around the central member, said sleeve having an inner surface and an outer surface and having openings on both ends thereof sized to receive the elongated central member into said sleeve so that said inner surface of said sleeve frictionally engages the elongated central member, the inner surface of said sleeve having a projecting portion adapted to engage a slot disposed on the elongated central member and whereby said sleeve is capable of sliding onto and off of the central member for reuse; and a raised pattern disposed on said outer surface of said sleeve.

* * * * *